United States Patent [19]
Voelkel

[11] Patent Number: 4,713,724
[45] Date of Patent: Dec. 15, 1987

[54] PORTABLE ION GENERATOR

[75] Inventor: Helmut Voelkel, Bayreuth, Fed. Rep. of Germany

[73] Assignee: HV Hofmann and Volkel, Bayreuth, Fed. Rep. of Germany

[21] Appl. No.: 880,064

[22] Filed: Jun. 30, 1986

[30] Foreign Application Priority Data

Jul. 20, 1985 [DE] Fed. Rep. of Germany ....... 3502021

[51] Int. Cl.$^4$ .......................... H01T 23/00; A61N 1/44
[52] U.S. Cl. ..................................... 361/231; 361/232; 128/202.25
[58] Field of Search .................................. 361/229–232, 361/212; 128/202.25; 55/103, 130, 146, 148, 152

[56] References Cited

U.S. PATENT DOCUMENTS 3,156,847 11/1964 Schweriner ........................ 361/230
3,818,269 6/1974 Stark ..................... 361/231
4,186,421 1/1980 Twitchett ....................... 361/229 X

FOREIGN PATENT DOCUMENTS 2521179 3/1977 Fed. Rep. of Germany .
2733729 9/1979 Fed. Rep. of Germany .
2535621 10/1981 Fed. Rep. of Germany .
2012137 3/1970 France ............................... 361/231
717242 10/1966 Italy ................................ 128/202.25
624302 7/1981 Switzerland .

Primary Examiner—L. T. Hix
Assistant Examiner—D. Rutledge
Attorney, Agent, or Firm—Robert J. Schaap

[57] ABSTRACT

A portable ion generator has a housing with a high-tension source disposed therein and a high-tension electrode of needle shape, projecting from the housing. The needle electrode is surrounded at a spacing therefrom by a second, annular electrode which is also connected to the high-tension source and which projects from the housing at the same side as the needle electrode. The housing is supported on an electrically conductive carrier element which is electrically conductively connected to the annular electrode.

8 Claims, 4 Drawing Figures

PORTABLE ION GENERATOR

BACKGROUND OF THE INVENTION

The present invention relates generally to an ion generator.

A portable ion generator is disclosed in German laid-open application (DE-OS) No. 28 22 228, comprising a high-tension source arranged in a housing, with a needle-shaped high-tension electrode projecting from the housing. That ion generator which serves as an antistatic device, provides that a periodic sequence of separate positive or negative charge pulses is generated, to ionise the ambient air. While the high-tension electrode which is electrically conductively connected to the high-tension source projects out of the housing, the counterelectrode which is at an electrical potential that is opposite to the high-tension electrode is simply formed in that arrangement by the ground potential of the electrical circuit for producing the high tension. The counterelectrode is therefore not of a specific configuration but is merely disposed in the interior of the housing so that when the generator is switched on, an electrical field is produced between the high-tension needle electrode and the housing. As mentioned above, that ion generator acts as an antistatic device for discharging static electricity on audio discs. It can also be used for discharging static electricity for example on papers which are used in electrostatic photocopiers, for removing static electricity from labels on plastic material surfaces, and for applying paint and primer agents to plastic material motor vehicle bodies.

In another form of ion generator as disclosed in German published specification (DE-AS) No. 25 21 179, a gas discharge lamp, in particular a fluorescent lamp, is to be connected to mains alternating voltage, which means that that ion generator can be used only in conjunction with a mains connection, as a quasi-stationary generator. As the ion generation rate decreases in an over-proportional manner, with increasing distance from the ion generator, the effectiveness of a stationary ion generator of that kind is satisfactory only in the direct vicinity thereof, its effectiveness at even a relatively small distance already leaving something to be desired. In order to improve its effectiveness at a greater distance, such an ion generator may be provided with a fan with which the ions generated can be transported over a greater distance. It will be appreciated however that fitting the ion generator with a fan in that way not only gives rise to a considerable amount of structural expenditure but also results in the ion generator being of a larger minimum size, in comparison with a corresponding ion generator without a fan.

Another form of ion generator for the ionisation of ambient air and other gases comprises a high-voltage transformer disposed in the generator housing and two rectifiers, as disclosed in German patent specification No. 2 535 621. In that ioniser, arranged on the high-voltage transformer is a tubular connecting member to which a negative or a positive voltage can be selectively applied. A spray needle unit for ionisation of ambient air or a container for a gas which in its interior may also be provided with a spray needle unit, may be fitted on to the connecting member. The last-mentioned construction of an ion generator with a container is used in particular to fill an injection syringe with positively or negatively ionised gas and to carry out intracutaneous injections with the injection syringe filled with ionised gas. Such intracutaneous injections are used in order to establish to which polarity of the injected ionised gas a patient responds (thus constituting a skin innoculation test). As that ion generator is to be used in conjunction with a gas bottle, it will be apparent that that ion generator is also a stationary item of equipment.

Still another form of ion generator includes a means for producing an air flow and also a means for generating ions, consisting of a tube connected to a high dc voltage, as well as having at least one grid which is disposed downstream of the tube on the air side and which is at a high negative potential, for catching any ions present, of opposite polarity, as disclosed in German published specification (DE-AS) No. 27 33 729. By virtue of using a specific means for producing an air flow, which in particular is in the form of a fan, that ion generator is also a stationary item of equipment with which it is possible to produce, in a room, an atmosphere which enhances the well-being of a person therein.

Swiss patent specification No. 624 302 discloses an apparatus for producing a dc voltage field in the human body. That apparatus comprises a housing having a high-tension source which in turn has a high-tension electrode and a counterelectrode. The high-tension electrode is in the form of a carrying or support element with which the apparatus can be supported or worn on the human body, preferably being in the form of a neck chain. In that apparatus, the counterelectrode is arranged in an electrically insulated fashion by virtue of its being provided in the interior of the housing of the apparatus, and cast into plastic material. The support element in the form of a neck chain is at one potential of the high-tension source, that is to say, the potential of the high-tension electrode, so that an electrical field which originates from the counterelectrode in the housing is produced in the region within the neck chain; that field does not provide for ionisation of the ambient air, but is intended to enhance the well-being of the person wearing the apparatus, as a result of the electrical field passing through the body of that person.

An apparatus for producing an ionised air jet is disclosed in German published specification (DE-AS) No. 12 81 602. That apparatus has a housing which is disposed around a conductive needle, wherein a conductive annular member is arranged on the housing at the air discharge opening of the apparatus and projects beyond said opening in such a way that an electrical discharge generated between the conductive needle and the air discharge opening by a high voltage embraces an element of volume which flares outwardly in a conical configuration in the housing. Therein the conductive needle is disposed on the axis of the bore of the housing and provided between the needle and the conductive annular member is a sleeve which comprises insulating material and which is extended conically outwardly at the air discharge opening. That apparatus is connected to a compressed air source in order to produce a sufficiently fast jet of air through the air discharge opening. With that apparatus it is possible to remove static charges from an object and at the same time to blow away from the surface of the object, particles of dust which are electrostatically attracted thereto. In addition that apparatus can neutralise static discharges both on the contaminating matter and also on the object to be cleaned.

SUMMARY OF THE INVENTION

An object of the present invention is to provide an ion generator which is independent of a mains connection and which is thus readily portable.

Another object of the present invention is to provide a portable ion generator for ionisation of particles which tend to flow towards the respiratory organs of the person using same and which can be attracted to the outside surface of the body of the person before such particles reach the respiratory organs.

Yet another object of the present invention is to provide a portable ion generator which can be used in close proximity of the respiratory organs of the person using the ion generator.

Still another object of the present invention is to provide a portable ion generator of compact size but with a high level of efficiency.

In accordance with the principles of the present invention, these and other objects are achieved by an ion generator comprising a housing accommodating a high-tension source, with a high-tension needle electrode projecting from the housing. The needle electrode is surrounded at a spacing by a counterelectrode which is also connected to the high-tension source and which projects from the housing at the same side thereof as the needle electrode. The housing is arranged on an electrically conductive support element electrically conductively connected to the counterelectrode.

By virtue of the counterelectrode being arranged in the vicinity of the high-tension needle electrode, an electrical field is produced between the two electrodes, in which particles such as dust, vegetable and blossom pollen and the like are ionised. By virtue of the support element which is electrically conductively connected to the counterelectrode and which comprises electrically conductive material, the outside surface of the body of the person using the ion generator, for example, wearing it suspended around the neck, is at the electrical potential of the counterelectrode so that the ionised particles are attracted to the surface of the body of the person wearing the ion generator, before they can penetrate in particular through the nostrils into the space in the nose and there give rise to allergic reactions. By virtue of the hightension needle electrode and the counterelectrode which is disposed therearound at a spacing therefrom, that arrangement also gives a directional characteristic in respect of the electrical field and thus the ions generated.

Therefore an ion generator according to the invention ion does not improve the climate of a room as a whole, but deliberately improves the specific area around the respiratory organs of the person using the ion generator. The ion generator is fitted with a high-voltage source which is powered by an accumulator, being operable to produce ions continuously. In that connection, the portable device may have a parallelepipedic or square housing of dimensions such that the device can be held in the hand, although the housing may alternatively be of a cylindrical or disc-like configuration.

The support element of electrically conductive material, which is electrically conductively connected to the counterelectrode, may be in the form of a fixing clip, fixing needle or pin, or the like.

In a preferred embodiment of an ion generator according to the invention, the support element is in the form of a neck chain. In that way the ion generator can be worn around the neck so that the needle electrode and the counterelectrode face towards the breathing organs, that is to say towards the nose and the mouth. An advantage of that ion generator configuration is that the hands remain free for other purposes while the ion generator is in use, because the ion generator does not need to be held in the hand.

Particularly in the case of an ion generator of the configuration last referred to, that is to say with a support means in the form of a neck chain, it is advantageous for the support element and the two electrodes of the device to be disposed at the same side of the housing. That side of the housing is preferably the top side of the device, which is towards the respiratory organs, specifically the nose and the mouth, so that the electrical field for ionising the particles between the two electrodes extends to those organs.

It has been found advantageous for the counter-electrode to be of an annular configuration and concentrically surround the needle electrode. The concentric arrangement of the counter-electrode which is of an annular configuration provides a symmetrical electrical field between the two electrodes when the device is switched on so that the ionisation of particles which may trigger off an allergic reaction is at an optimum, while the ionised particles do not reach the respiratory organs but are diverted to the surface of the body of the person wearing the ion generator, before such particles can reach the nose and mouth of that person.

In that arrangement, the annular counterelectrode is preferably disposed in a plane, while the needle electrode is disposed perpendicularly to the plane in which the counterelectrode is disposed. In that embodiment the counterelectrode is preferably at a spacing from the housing, which is greater than the spacing of the tip of the needle electrode from the housing. That means that the annular counterelectrode, in a direction towards the tip of the tapering needle electrode, is arranged in front of the tip thereof. By virtue of such a configuration, the needle electrode is protected from being touched, thereby eliminating the possible risk of injury by the needle electrode.

In another embodiment of the ion generator according to the invention, the needle electrode and the counterelectrode are arranged in a recess in the housing in such a way that they do not project from the surface of the housing which surrounds the recess. That configuration of the ion generator also gives good protection from contact with the needle electrode, besides also affording optimum ionisation of particles by the annular counterelectrode concentrically around the needle electrode.

It has been found that the ion generator according to the invention can be satisfactorily used for protecting people who have an allergic reaction to small particles such as vegetable-matter particles. It has been found for example that people who are allergic to blossom pollen and who react thereto with what is called hay fever, are rendered at least substantially insensitive to air-borne pollen when using an ion generator according to the invention.

Further objects, features and advantages of the invention will be apparent from the following description of two embodiments of ion generators according to the invention.

DESCRIPTION OF THE PREFERRED EMBODIMENTS

Figures 1, 2, 3, 4:
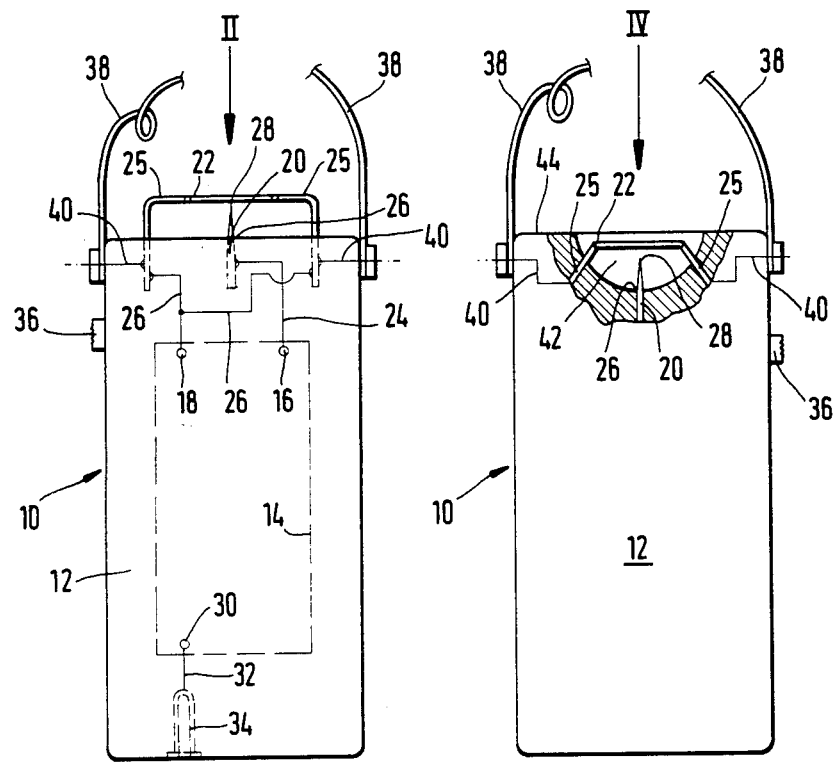
FIG. 1 is a front view of a first embodiment of an ion generator.
FIG. 2 is a plan view of the ion generator shown in FIG. 1, viewing in the direction indicated by arrow II in FIG. 1.
FIG. 3 shows another embodiment of an ion generator, in partly cut-away form.
FIG. 4 is a plan view of the ion generator shown in FIG. 3, viewing in the direction indicated by the arrow IV in FIG. 3.

Referring firstly to FIGS. 1 and 2, shown therein is an ion generator 10 in the form of a portable device of compact size. The ion generator 10 comprises a parallelepipedic housing 12 in which there is disposed a dc high-tension source 14 which is shown in broken lines in FIG. 1, powered by an accumulator (not shown). The source 14 is electrically conductively connected by its outputs 16 and 18 to a needle-shaped high-tension electrode 20 and a counterelectrode 22 respectively. The electrically conductive connection between the outputs 16 and 18 and the two electrodes 20 and 22 is indicated diagrammatically by connecting wires 24 and 26.

As can be seen from FIG. 2, the counterelectrode 22 is disposed concentrically around the needle electrode 20. The counterelectrode 22 is thus of an annular configuration and is arranged by means of holder members 25 at a spacing from the housing 12 of the ion generator 10.

As shown in FIG. 1, the annular counterelectrode 22 is disposed in a plane which is at a larger spacing from the base 26 of the needle electrode 20, than the spacing of the tip 28 of the needle electrode from the base 26. In that way the counterelectrode 22 also serves as a contact guard, thereby eliminating injuries which could possibly be caused by contact with the needle electrode 20.

Reference numeral 30 denotes an input of the source 14, which is electrically conductively connected by way of a connecting line 32 to a connecting jack 34 in the housing 12 of the ion generator 10. By means of the connecting jack 34 it is possible for the accumulator (not shown) provided in the source 14 to be charged up again when required. A switch whose operating member 36 projects from the side of the housing 12 of the ion generator 10 is provided for switching the ion generator on and off.

Mounted to the housing 12 is a carrier or support element 38 in the form of a neck chain or necklace member of which only a portion is shown in FIGS. 1 and 2. The support element 38 comprises electrically conductive material and is electrically conductively connected to the counterelectrode 22 by means of connecting lines 40 so that the outside surface of the body of a person wearing the ion generator around the neck by means of the support element 38 is at the electrical potential of the counterelectrode 22.

As can be clearly seen from FIG. 1, the support element 38 in the form of a neck chain and the two electrodes 20 and 22 of the ion generator 10 are arranged at the same side of the housing 12 as the neck chain. That provides that, when the ion generator is worn around the neck, the electrical field which is generated between the two electrodes 20 and 22 is directed towards the respiratory organs, that is to say towards the mouth and the nose, thereby optimising ionisation of particles flowing towards those organs. The ionised particles are then attracted to the surface of the body before they can pass into the nose and mouth and in particular into the space within the nose.

Reference will now be made to FIGS. 3 and 4 showing another embodiment of an ion generator 10 according to the invention, with a portable parallelepipedic housing 12. The dc high-tension source disposed in the housing 12 as well as the connection of the high-tension source to the electrode 20 and the counterelectrode 22 are not shown in FIG. 3 or FIG. 4 but it corresponds to the arrangement illustrated in FIG. 1. The embodiment of the ion generator 10 shown in FIGS. 3 and 4 also provides that the counterelectrode 22 is mounted on holder members 25 in such a way that the annular counterelectrode 22 is disposed concentrically around the needle electrode 20. In this embodiment also the annular counterelectrode 22 is disposed in a plane which is at a greater spacing than the tip 28 of the electrode 20, from the base 26 thereof. In this arrangement also, that provides for protection from contact with the sharp needle electrode 20. The same purpose is also served by the two electrodes 20 and 22 being arranged in a dish-like recess 42 in the top surface of the housing 12 in such a way that the electrodes 20 and 22 do not project beyond the surface 44 of the housing 12, which surrounds and delimits the recess 42.

Reference numeral 38 in FIGS. 3 and 4 also denotes an electrically conductive support or carrier element, of which a portion is shown, in the form of a necklace member or neck chain. An electrically conductive connection between the support element 38 and the counterelectrode 22 is made by connecting wires 40, while a switch whose operating member is shown at 36 is again provided for switching the ion generator on and off.

The housing 12 does not have to be parallelepipedic but may be of a cylindrical, disc or like configuration.

The source 14 is not shown in detail in the drawing and is also not described in greater detail herein because it is for example a known high-tension source having a cascade circuit of diodes and capacitors.

It will be appareciated that the above-described embodiments of the ion generator were only described by way of example of the invention and that various modifications may be made therein without thereby departing from the scope of the invention.

I claim:

1. A portable ion generator comprising a housing, a high-tension source in the housing, a high-tension needle electrode connected to said source and arranged to project from the housing, a counterelectrode arranged to project from the housing at the same side as the needle electrode and disposed around said needle electrode at a spacing therefrom, means connecting said counterelectrode to said source, an electrically conductive support element, and means electrically conductively connecting said support element to said counterelectrode.

2. An ion generator as set forth in claim 1 wherein said support element is in the form of a necklace means.

3. An ion generator as set forth in claim 1 wherein said support element and said needle electrode and said counterelectrode are arranged at the same side of said housing.

4. An ion generator as set forth in claim 1 wherein said counterelectrode is of an annular configuration and concentrically surrounds said needle electrode.

5. An ion generator as set forth in claim 4 wherein said annular counterelectrode extends substantially in a plane and said needle electrode is oriented in substantially perpendicular relationship to said plane in which said counterelectrode is disposed.

6. An ion generator as set forth in claim 5 wherein said counterelectrode is at a spacing from said housing, which is greater than the spacing of the tip of said needle electrode from said housing.

7. An ion generator as set forth in claim 1 wherein said housing is shaped to define a recess in the outside surface thereof and wherein said needle electrode and said counterelectrode are arranged in said recess in such a way that they do not project beyond said surface of said housing in which said recess is provided.

8. A portable ion generator comprising a housing, a high-tension source disposed in the housing and having first and second outputs, a high-tension needle electrode carried by the housing and projecting therefrom, means electrically conductively connecting said needle electrode to the first output of said source, a counterelectrode carried by said housing adjacent said needle electrode and of such a configuration as to extend at least substantially around said needle electrode at a spacing therefrom, means connecting said counterelectrode to the second output of said source, an electrically conductive necklace means connected to said housing and arranged to be worn around the neck of a user of the ion generator, adapted to support said housing with said needle electrode and said counterelectrode facing generally towards the external respiratory organs of said person, and means electrically conductively connecting said necklace means to said counterelectrode.

* * * * *